United States Patent
Chen et al.

(10) Patent No.: US 11,324,677 B1
(45) Date of Patent: May 10, 2022

(54) ORAL CARE WHITENING COMPOSITIONS

(71) Applicant: Colgate-Palmolive Company, New York, NY (US)

(72) Inventors: Xiang Chen, Somerset, NJ (US); Suman Chopra, Monroe, NJ (US); Lin Fei, Kendall Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/519,931

(22) Filed: Nov. 5, 2021

Related U.S. Application Data

(60) Provisional application No. 63/110,586, filed on Nov. 6, 2020.

(51) Int. Cl.

| | |
|---|---|
| *A61K 8/22* | (2006.01) |
| *A61K 8/86* | (2006.01) |
| *A61K 8/81* | (2006.01) |
| *A61K 8/24* | (2006.01) |
| *A61Q 11/00* | (2006.01) |
| *A61K 8/21* | (2006.01) |

(52) U.S. Cl.
CPC ............... *A61K 8/22* (2013.01); *A61K 8/21* (2013.01); *A61K 8/24* (2013.01); *A61K 8/8176* (2013.01); *A61K 8/86* (2013.01); *A61Q 11/00* (2013.01); *A61K 2800/48* (2013.01)

(58) Field of Classification Search
CPC ........ A61Q 11/00; A61K 8/22; A61K 31/327; A61K 22/40
USPC ...................... 424/49, 53; 433/215
See application file for complete search history.

(56) References Cited

U.S. PATENT DOCUMENTS

| | | | | |
|---|---|---|---|---|
| 7,025,950 B2 * | 4/2006 | Majeti | .................... | A61K 8/893 424/49 |
| 7,166,235 B2 * | 1/2007 | Majeti | .................... | A61K 8/891 252/8.57 |
| 2006/0099155 A1 * | 5/2006 | MacDonald | ........... | A61Q 11/00 424/53 |
| 2007/0071695 A1 * | 3/2007 | Chopra | .................... | A61K 8/25 424/53 |
| 2007/0071696 A1 | 3/2007 | Wang et al. | | |
| 2014/0377193 A1 * | 12/2014 | Chopra | .................. | A61Q 11/00 424/57 |

FOREIGN PATENT DOCUMENTS

| | | |
|---|---|---|
| CA | 2830684 | 4/2007 |
| EP | 3086861 | 11/2016 |
| WO | 2014/092735 | 6/2014 |
| WO | 2014/092736 | 6/2014 |
| WO | 2019/108194 | 6/2019 |
| WO | 2019/108202 | 6/2019 |
| WO | 2019/117885 | 6/2019 |

OTHER PUBLICATIONS

International Search Report and Written Opinion of the International Searching Authority in International Application No. PCT/US2021/058202, dated Feb. 24, 2022.

* cited by examiner

*Primary Examiner* — Walter E Webb

(57) ABSTRACT

Disclosed herein are oral care compositions comprising a peroxide whitening complex in an amount to provide from 3.5% to 7% of hydrogen peroxide by weight of the composition, and a block copolymer of ethylene oxide and propylene oxide in an amount of from 40% to 60% by weight of the composition. Methods of making and using the dentifrices are also provided.

20 Claims, 1 Drawing Sheet

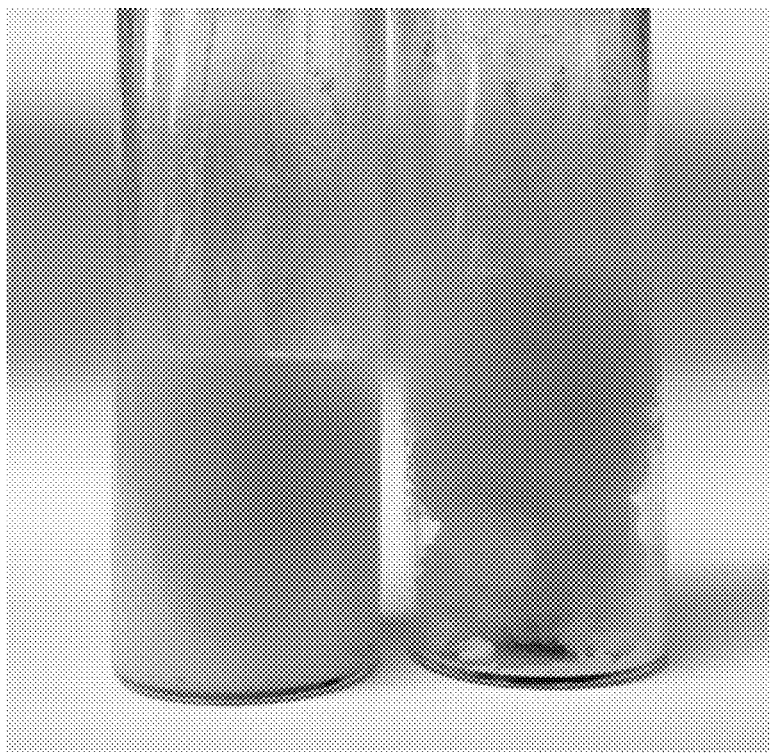

ORAL CARE WHITENING COMPOSITIONS

BACKGROUND

Conventional oral care products (e.g., toothpastes, gels, etc.) containing whitening agents are often utilized to whiten teeth. For example, conventional toothpastes containing peroxides (e.g., hydrogen peroxide) are often utilized to oxidize chromophores bound to surfaces of teeth to thereby whiten the teeth. However, peroxide compounds are highly reactive, and consequently difficult to formulate. Moreover, hydrogen peroxide can spontaneously decompose to form oxygen gas (0$_2$) and water, so that on storage, the dentifrice container may bloat, burst, or leak, and the remaining formulation will not have enough peroxide remaining to clean and whiten teeth effectively. Some dentifrices initially comprise very high levels of peroxide, which decomposes over time, so that the exact amount of peroxide delivered on application is variable and largely depends on how long and under what conditions the dentifrice has been stored.

The peroxide may be present as hydrogen peroxide or as a source of bound hydrogen peroxide. Sources of bound hydrogen peroxide include PVP-H$_2$O$_2$ complexes, urea peroxide, calcium peroxide and sodium percarbonate. The commonly used humectants in toothpaste, such as propylene glycol, PEG, glycerin, sorbitol, interact with PVP-H$_2$O$_2$ complexes differently, resulting in different degree of the instability of peroxide. Among them propylene glycol is commonly used as the major carrier in formulations containing PVP-H$_2$O$_2$ complexes due to its least interaction with PVP-H$_2$O$_2$ complexes. However, it has been a challenge to formulate stable whitening toothpaste compositions with a high amount of PVP-H$_2$O$_2$ complexes (e.g., providing 4% hydrogen peroxide).

There is a need for peroxide-containing whitening oral care compositions containing a high amount of PVP-H$_2$O$_2$ complexes which exhibit improved whitening efficacy and stability.

BRIEF SUMMARY

In an aspect, the invention provides an oral care composition comprising a peroxide whitening complex in an amount to provide from 3.5% to 7% of hydrogen peroxide by weight of the composition, and a block copolymer of ethylene oxide and propylene oxide in an amount of from 40% to 60% by weight of the composition. The block copolymer of ethylene oxide and propylene oxide may have a molecular weight of from 1,000 Da to 3,000 Da. In some embodiments, the composition does not contain propylene glycol. In some embodiments, the whitening complex comprises a cross-linked polyvinylpyrrolidone complexed with hydrogen peroxide (PVP-H$_2$O$_2$). In some embodiments, the composition comprises a fluoride ion source.

In another aspect, the invention provides a method of whitening teeth, comprising applying any of the oral care compositions disclosed herein to the surface of the teeth.

In another aspect, the invention provides the use of a block copolymer of ethylene oxide and propylene oxide for increasing the stability of an oral care composition comprising a peroxide whitening complex in an amount to provide from 3.5% to 7% of hydrogen peroxide by weight of the composition, wherein the block copolymer of ethylene oxide and propylene oxide is present in an amount of from 40% to 60% by weight of the composition. The block copolymer of ethylene oxide and propylene oxide may have a molecular weight of from 1,000 Da to 3,000 Da. In some embodiments, the composition does not contain propylene glycol. In some embodiments, the whitening complex comprises a cross-linked polyvinylpyrrolidone complexed with hydrogen peroxide (PVP-H$_2$O$_2$).

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

FIG. 1 shows a photo of PVP-H$_2$O$_2$ mixed with PLURONIC® L35 (left vial) or propylene glycol (right vial).

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention relates to stable oral care whitening compositions containing a high level (e.g., about 4%) of hydrogen peroxide. Although humectants such as propylene glycol can be used as the main carrier to formulate stable oral care compositions comprising PVP-H$_2$O$_2$ complexes in an amount to provide up to 3% hydrogen peroxide, formulating stable oral care composition comprising a higher amount of PVP-H$_2$O$_2$ complexes has been challenging. PVP-H$_2$O$_2$ complex has a load limit in the amount of hydrogen peroxide the complex can carry. For example, Peroxydone™ XL-10 complex contains about 18% hydrogen peroxide. Thus, 22% Peroxydone™ XL-10 has to be added into an oral care composition to deliver 4% hydrogen peroxide. However, the high level of cross-linked PVP present in 22% Peroxydone™ XL-10 thickens the formulation unacceptably over time in a propylene glycol based formulation. In the present invention, the present inventors have found that the complete replacement of propylene glycol with a block copolymer of ethylene oxide and propylene oxide (e.g., PLURONIC® L35) improves the stability of an oral care composition containing 22% Peroxydone™ XL-10. It has also been found that hydrogen peroxide and fluoride are stable over time in the block copolymer of ethylene oxide and propylene oxide (e.g., PLURONIC® L35)-based formulation.

The invention provides, in an aspect, an oral care composition (Composition 1.0) comprising a peroxide whitening complex in an amount to provide from 3.5% to 7% of hydrogen peroxide by weight of the composition, and a block copolymer of ethylene oxide and propylene oxide in an amount of from 40% to 60% by weight of the composition.

For example, the invention includes:

1.1. Composition 1.0, wherein the whitening complex comprises or is a cross-linked polyvinylpyrrolidone complexed with hydrogen peroxide (PVP-$H_2O_2$).
1.2. Composition 1.0 or 1.1, wherein the whitening complex contains 10-30% hydrogen peroxide, based on the weight of the whitening complex, e.g., 15-25%, 15-20%, or about 18%.
1.3. Any of preceding compositions, wherein the peroxide whitening complex is present in an amount to provide 3.5-6%, e.g., 3.5-5%, 3.5-4.5%, 3.8-4.2%, 3.9%-4.1%, or about 4%, of hydrogen peroxide, by weight of the composition.
1.4. Any of preceding compositions, wherein the block copolymer of ethylene oxide and propylene oxide is represented by formula (ethylene oxide)$_x$-(propylene oxide)$_y$-(ethylene oxide)$_z$, wherein:
  x is an integer from about 5 to about 15,
  y is an integer from about 10 to about 20, and
  z is an integer from about 5 to about 15.
1.5. Any of preceding compositions, wherein the block copolymer of ethylene oxide and propylene oxide is represented by formula (ethylene oxide)$_{11}$-(propylene oxide)$_{16}$-(ethylene oxide)$_{11}$.
1.6. Any of preceding compositions, wherein the block copolymer of ethylene oxide and propylene oxide has an average molecular weight of from 1,000 Da to 3,000 Da, e.g., from 1,500 Da to 2,500 Da, from 1,700 Da to 2,200, from 1,800 to 2,000, or about 1,900 Da.
1.7. Any of preceding compositions, wherein the block copolymer of ethylene oxide and propylene oxide is present in an amount of from 40% to 50%, e.g., from 45% to 50%, from 44% to 50%, from 46 to 48%, from 44% to 48%, or from 44% to 47%, by weight of the composition.
1.8. Any of preceding compositions, wherein the composition does not contain propylene glycol.
1.9. Any of preceding compositions, wherein the composition does not contain any of propylene glycol, glycerin, sorbitol and polyethyleneglycol (PEG).
1.10. Any of preceding compositions, wherein the composition comprise a thickening agent selected from fumed silica, colloidal silica, cetearyl alcohol, or a combination thereof, optionally in an amount of from 0.5% to 5%, e.g., from 1% to 4%, from 1% to 3%, from 1% to 2%, about 1.5%, by weight of the composition, optionally wherein the composition comprises a fumed silica.
1.11. Any of preceding compositions, wherein the composition comprises an ethylene oxide, propylene oxide block co-polymer having an average molecular weight of greater than 5000 Da, e.g., 8000-13000 Da, e.g., about 9800 Da, optionally wherein the ethylene oxide, propylene oxide block co-polymer is present in an amount of from 5% to 10%, e.g., from 6% to 9%, from 7% to 8%, or about 7.5%, by weight of the composition.
1.12. Any of preceding compositions, wherein the composition comprises an abrasive selected from sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, or mixtures thereof.
1.13. Any of preceding compositions, wherein the composition comprises calcium pyrophosphate.
1.14. Compositions 1.12 or 1.13, wherein the abrasive is present in an amount of from 5% to 40%, e.g., 5-30%, 5-20%, 10-30%, 10-20%, 12-18%, 13-17%, or about 15%, by weight of the composition.
1.15. Any of preceding compositions, wherein the composition comprises an anionic surfactant, e.g., a surfactant selected from sodium lauryl sulfate, sodium ether lauryl sulfate, and a combination thereof.
1.16. Composition 1.15, wherein the anionic surfactant is sodium lauryl sulfate.
1.17. Composition 1.15 or 1.16, wherein the anionic surfactant is present in an amount of from 0.3% to 4.5%, e.g., 1-3%, 1.5-2.5%, 1.8-2.2%, or about 2%, by weight of the composition.
1.18. Any of preceding compositions, wherein the composition comprises a fluoride ion source.
1.19. Composition 1.18, wherein the fluoride ion source is selected from sodium fluoride, stannous fluoride, potassium fluoride, sodium monofluorophosphate, sodium fluorosilicate, ammonium fluorosilicate, amine fluoride (e.g., N'-octadecyltrimethylenediamine-N,N,N'-tris(2-ethanol)-dihydrofluoride), ammonium fluoride, titanium fluoride, hexafluorosulfate, and a combination thereof.
1.20. Composition 1.18 or 1.19, wherein the fluoride ion source is present in an amount sufficient to supply 25 ppm to 5,000 ppm of fluoride ions, generally at least 500 ppm, e.g., 500 to 2000 ppm, e.g., 1000 ppm to 1600 ppm, e.g., 1450 ppm.
1.21. Any of Compositions 1.18-1.20, wherein the fluoride ion source is sodium monofluorophosphate or sodium fluoride.
1.22. Any of preceding compositions, wherein the oral care composition comprises an anticalculus agent, optionally wherein anticalculus agent is selected from tetrasodium pyrophosphate (TSPP), sodium tripolyphosphate (STPP), or a combination thereof.
1.23. Any of preceding compositions, wherein the oral care composition comprises sodium acid pyrophosphate ($Na_2H_2P_2O_7$), optionally wherein sodium acid pyrophosphate is present in an amount of from 0.1% to 5%, e.g., from 0.1% to 3%, from 0.1% to 2%, from 0.1% to 1%, from 0.1% to 0.5%, from 0.2% to 0.5%, from 0.3% to 0.5%, or about 0.4%, by weight of the composition.
1.24. Any of the preceding compositions, wherein the composition comprises a basic amino acid in free or salt form.
1.25. Composition 1.24, wherein the basic amino acid comprises one or more of arginine, lysine, citrulline, ornithine, creatine, histidine, diaminobutanoic acid, diaminoproprionic acid, salts thereof, or combinations thereof.
1.26. Composition 1.24 or 1.25, wherein the basic amino acid has the L-configuration.
1.27. Any of Compositions 1.24-1.26, wherein the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.
1.28. Any of Compositions 1.24-1.27, wherein the basic amino acid comprises arginine.
1.29. Composition 1.28, wherein the basic amino acid comprises L-arginine.
1.30. Composition 1.28 or 1.29, wherein the basic amino acid comprises arginine bicarbonate, arginine phosphate, arginine sulfate, arginine hydrochloride or combinations thereof, optionally wherein the basic amino acid is arginine bicarbonate.
1.31. Any of the preceding compositions, the composition comprises a zinc ion source.
1.32. Composition 1.31, wherein the zinc ion source is selected from the group consisting of zinc oxide, zinc sulfate, zinc chloride, zinc citrate, zinc lactate, zinc gluconate, zinc malate, zinc tartrate, zinc carbonate, zinc phosphate and a combination thereof.
1.33. Composition 1.31 or 1.32, wherein the zinc ion source is present an amount of from 0.01% to 5%, e.g., 0.1% to 4%, or 0.5% to 3%, by weight of the composition.
1.34. Any of Compositions 1.31 to 1.33, wherein the additional zinc ion source is selected from the group consisting of zinc oxide, zinc citrate, and a combination thereof.
1.35. Any of Compositions 1.31-1.34, wherein the zinc ion source is a combination of zinc oxide and zinc citrate.
1.36. Any of the preceding compositions, wherein the composition comprises a stannous ion source, optionally wherein the stannous ion source is selected from the group consisting of stannous chloride, stannous fluoride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof.
1.37. Any of the preceding compositions, wherein the composition is free or substantially free of water, optionally wherein water is present in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition, and further optionally wherein the composition does not contain water.
1.38. Any of the preceding compositions, wherein the composition comprises an effective amount of one or more antibacterial agents, optionally wherein the antibacterial agent is selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures thereof; e.g., triclosan or cetylpyridinium chloride.
1.39. Any of the preceding compositions, wherein the composition comprises a physiologically or orally acceptable potassium salt, e.g., potassium nitrate or potassium chloride, in an amount effective to reduce dentinal sensitivity.
1.40. Any of the preceding compositions, wherein the composition comprises a sweetener, optionally wherein the composition comprises sodium saccharin and sucralose, and further optionally wherein the composition comprises a triple sweetener system of sodium saccharin, sucralose and rebaudioside M (Reb M).
1.41. Any of the preceding compositions, wherein the composition comprises a breath freshener, fragrance or flavoring.
1.42. Any of the preceding compositions, further comprising an oral care ingredient selected from: a film; a colorant; a pH modifying agent; and a sensitivity reducing agent.
1.43. Any of the preceding compositions, wherein the composition is a toothpaste or gel.

The oral care composition of the present invention may be free or substantially free of water. As used herein, the term "substantially free of water" may refer to a composition that contains water in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition. In some embodiments, the oral care composition is anhydrous. In some embodiments, the oral care composition does not contain water.

The oral care composition of the present invention may be a single phase oral care composition. For example, the peroxide whitening agent, the block copolymer of ethylene oxide and propylene oxide and all other ingredients of the composition may be maintained together with one another in a single phase and/or vessel. For example, the peroxide whitening agent, the block copolymer of ethylene oxide and propylene oxide and all other ingredients of the composition may be maintained together with one another in a single phase such as a single homogenous phase. The single homogenous phase may be an anhydrous composition.

The oral care composition may form at least a portion of or be used in one or more oral care products. The oral care composition may include or be combined with an orally acceptable vehicle to form the oral care product (e.g., toothpaste). Illustrative oral care products may include, but are not limited to, a toothpaste (dentifrice), a prophylactic paste, a tooth powder, a tooth polish, a tooth gel (e.g., whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may form at least a portion of or be used with a toothpaste. For example, the oral care composition may typically be a gel of the toothpaste, or a whitening gel to be combined with the toothpaste. The oral care composition may include or be combined with an orally acceptable vehicle to form the oral care product. In some embodiments, the oral care composition is a toothpaste or gel.

The oral care composition of the present invention comprises a peroxide whitening complex which acts as a source of bound hydrogen peroxide. The whitening complex may contain 10-30% hydrogen peroxide, based on the weight of the whitening complex, e.g., 15-25%, 15-20%, or about 18%. In some embodiments, the total amount of hydrogen peroxide is 3.5-7% based on the weight of the composition, e.g., 3.5-6%, 3.5-5%, 3.5-4.5%, 3.8-4.2%, 3-9-4.1%, or about 4%. Peroxide may be bound to a polymer such as PVP (polyvinylpyrrolidone). In some embodiments, the peroxide whitening complex is a cross-linked polyvinylpyrrolidone complexed with hydrogen peroxide (PVP-$H_2O_2$), e.g., Peroxydone™ XL-10 (Ashland Specialty Chemical).

The oral care composition of the present invention comprises a block copolymer of ethylene oxide (EO) and propylene oxide (PO). The block copolymers of ethylene oxide and propylene oxide may be nonionic. For example, the block copolymers of ethylene oxide and propylene oxide may be a nonionic surfactant. The block copolymers of ethylene oxide and propylene oxide may be represented by formula (1).

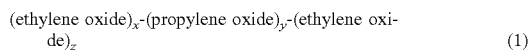

(ethylene oxide)$_x$-(propylene oxide)$_y$-(ethylene oxide)$_z$ (1)

where x may be an integer of from about 5 to about 15 (e.g., x=9-13, or about 11), y may be an integer from about 10 to about 20 (e.g., y=13-17, or about 16), and z may be an integer from about 5 to about 15 (e.g., x=9-13, or about 11). In a certain embodiment, the block copolymer of ethylene oxide and propylene oxide may be represented by formula (2).

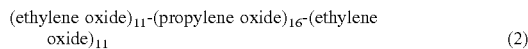

(ethylene oxide)$_{11}$-(propylene oxide)$_{16}$-(ethylene oxide)$_{11}$ (2)

The block copolymer of ethylene oxide and propylene oxide may have an average molecular weight of from about 1,000 Da to about 3,000 Da. For example, the block copolymer of ethylene oxide and propylene oxide may have an average molecular weight of from about 1,000 Da, about 1,100 Da, about 1,200 Da, about 1,300 Da, about 1,400 Da, about 1,500 Da, about 1,600 Da, about 1,700 Da, about 1,800 Da, or about 1,850 Da to about 1,950 Da, about 2,000 Da, about 2,100 Da, about 2,200 Da, about 2,300 Da, about 2,400 Da, about 2,500 Da, about 2,600 Da, about 2,700 Da, about 2,800 Da, about 2,900 Da, or about 3,000 Da. In another example, the block copolymer of ethylene oxide and propylene oxide may have an average molecular weight of from about 1,000 Da to about 2,800 Da, about 1,100 Da to about 2,700 Da, about 1,200 Da to about 2,600 Da, about 1,300 Da to about 2,500 Da, about 1,400 Da to about 2,400 Da, about 1,500 Da to about 2,300 Da, about 1,600 Da to about 2,200 Da, about 1,700 Da to about 2,100 Da, about 1,800 Da to about 2,000 Da, or about 1,850 Da to about 1,950 Da. In some embodiments, the block copolymer of ethylene oxide and propylene oxide may have an average molecular weight of from about 1,850 Da to about 1,950 Da, e.g., about 1,900 Da.

Illustrative block copolymers of ethylene oxide (EO) and propylene oxide (PO) may be or include, but are not limited to, PLURONIC® L35, PLURONIC® LI, PLURONIC® L43, PLURONIC® L10, PLURONIC® L44, PLURONIC® 10R5, PLURONIC® 17R4, PLURONIC® L25R4, PLURONIC® P84, PLURONIC® P65, PLURONIC® PI 04, PLURONIC® PI 05, and the like, and combinations thereof, all of which are commercially available from BASF of Mount Olive, N.J. In a certain embodiment, the block copolymer of ethylene oxide and propylene oxide is PLURONIC® L35.

The block copolymer of ethylene oxide and propylene oxide may be present in an amount of from 40% to 60% by weight of the composition. In some embodiments, the block copolymer of ethylene oxide and propylene oxide is present in an amount of from 40% to 50%, e.g., from 45% to 50%, from 44% to 50%, from 46 to 48%, from 44% to 48%, or from 44% to 47%, by weight of the composition.

In some embodiments, the composition does not contain propylene glycol. In some embodiment, the composition does not contain any of propylene glycol, glycerin, sorbitol and polyethyleneglycol (PEG).

The composition of the present invention may comprise a thickening agent selected from fumed silica, colloidal silica, cetearyl alcohol, or a combination thereof in an amount of from 0.5% to 5%, e.g., from 1% to 3%, from 1% to 2%, about 1.5%, by weight of the composition. In some embodiments, the composition comprises a fumed silica.

In some embodiments, the oral care composition may comprise polymers and/or copolymers of polyethylene glycol, of ethylene oxide/propylene oxide, and of silicone. If such copolymers/polymers are used, they may be selected from commercially available materials. In some embodiments, such block copolymer is an ethylene oxide, propylene oxide block co-polymer of formula (ethylene oxide)$_x$-(propylene oxide)$_y$, wherein x is an integer of 80-150, e.g., 100-130, e.g., about 116 or about 118, and y is an integer 30-80, e.g., about 60-70, e.g., about 66, having an average molecular weight of greater than 5000 Da, e.g., 8000-13000 Da, e.g., about 9800 Da. An illustrative ethylene oxide, propylene oxide block co-polymer is PLURACARE® L1220 (available from BASF, Wyandotte, Mich., United States of America). In some embodiments, the ethylene oxide, propylene oxide block co-polymer is present in an amount of from 5% to 10%, e.g., from 6% to 9%, from 7% to 8%, or about 7.5%, by weight of the composition.

In some embodiment, the oral care composition of the present invention may have a viscosity of about 10,000 CPS to about 700,000 CPS, preferably about 30,000 CPS to about 300,000 CPS.

The oral care composition of the present invention may include an abrasive system including one or more abrasives. As used herein, the term "abrasive" may also refer to materials commonly referred to as "polishing agents". Illustrative abrasives may include, but are not limited to, one or more phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, and the like, and mixtures or combinations thereof. In some embodiments, the abrasives may include a combination of one or more phosphate salts and an additional abrasive. Illustrative abrasives that may be combined with the phosphate salts may be or include, but are not limited to, calcium carbonate, magnesium carbonate, hydrated alumina, silica, zirconium silicate, aluminum silicate including calcined aluminum silicate, polymethyl methacrylate, and the like, and mixtures or combinations thereof. In some embodiments, the abrasive system includes a combination of abrasives. For example, the abrasive system may comprise a combination of sodium metaphosphate and calcium pyrophosphate. In a certain embodiment, the abrasive system comprises calcium pyrophosphate in some embodiments, the amount or concentration of the abrasives may be from 5% to 40%, e.g., 5-30%, 5-20%, 10-30%, 10-20%, 12-18%, 13-17%, or about 15%, by weight of the composition.

The oral care composition of the present invention may comprise an additional surfactant other than the block copolymer of ethylene oxide and propylene oxide. In some embodiments, the oral care composition may comprise an anionic surfactant. Suitable anionic surfactants include without limitation water-soluble salts of C8-20 alkyl sulfates, sulfonated monoglycerides of C8-20 fatty acids, sarcosinates, taurates and the like. Illustrative examples of these and other classes include sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isethionate, sodium laureth carboxylate, and sodium dodecyl benzenesulfonate. In some embodiments, the anionic surfactant is sodium lauryl sulfate (SLS). The anionic surfactant, e.g., sodium lauryl sulfate, may be present in an amount of from 0.3% to 4.5% by weight, e.g., 1-3%, 1.5-2.5%, 1.8-2.2%, or about 2%, by weight of the composition.

The oral care composition of the present invention may comprise fluoride such as one or more fluoride ion sources (e.g., soluble fluoride salts). A wide variety of fluoride ion-yielding materials may be employed as sources of soluble fluoride. Illustrative fluoride ion sources include, but are not limited to, sodium fluoride, stannous fluoride, potassium fluoride, sodium monofluorophosphate, fluorosilicate salts, such as sodium fluorosilicate and ammonium fluorosilicate, amine fluoride, ammonium fluoride, and combinations thereof. In some embodiment, the fluoride ion source is sodium monofluorophosphate or sodium fluoride. The amount of the fluoride ion source present in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to supply 25 ppm to 5,000 ppm of fluoride ions, generally at least 500 ppm, e.g., 500 to 2000 ppm, e.g., 1000 ppm to 1600 ppm, e.g., 1450 ppm.

The oral care composition of the present invention may comprise anticalculus agents. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent comprises tetrasodium pyrophosphate (TSPP), sodium tripolyphosphate (STPP), or a combination thereof.

The oral care composition of the present invention may comprise sodium acid pyrophosphate ($Na_2H_2P_2O_7$). In some embodiments, sodium acid pyrophosphate ($Na_2H_2P_2O_7$) may be present in an amount of from 0.1% to 5%, e.g., from 0.1% to 3%, from 0.1% to 2%, from 0.1% to 1%, from 0.1% to 0.5%, from 0.2% to 0.5%, from 0.3% to 0.5%, or about 0.4%, by weight of the composition.

The oral care composition of the present invention may comprise a basic amino acid in free or salt form. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrulline, ornithine, creatine, histidine, diaminobutyric acid, diaminopropionic acid, salts thereof or combinations thereof. In a particular embodiment, the basic amino acids are selected from arginine, lysine, citrulline, and ornithine. The basic amino acids of the oral care composition may generally be present in the L-form or L-configuration. The basic amino acids may be provided as a salt of a di- or tri-peptide including the amino acid. In some embodiments, at least a portion of the basic amino acid present in the oral care composition is in the salt form. In some embodiments, the basic amino acid is arginine, for example, L-arginine, or a salt thereof. Arginine may be provided as free arginine or a salt thereof. For example, Arginine may be provided as arginine phosphate, arginine hydrochloride, arginine sulfate, arginine bicarbonate, or the like, and mixtures or combinations thereof. The basic amino acid may be provided as a solution or a solid. For example, the basic amino acid may be provided as an aqueous solution. In some embodiment, the amino acid includes or is provided by an arginine bicarbonate solution. For example, the amino acid may be provided by an about 40% solution of the basic amino acid, such as arginine bicarbonate or alternatively called as arginine carbamate. In some embodiments, the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.

The oral care composition of the present invention may comprise a zinc ion source. The zinc ion source may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc picolinate, zinc propionate, zinc salicylate, zinc silicate, zinc stearate, zinc tartrate, zinc undecylenate, and mixtures thereof. In some embodiments, the zinc ion source is present in an amount of from 0.01. % to 5%, e.g., 0.1% to 4%, or 1% to 3%, by weight of the composition.

The oral care composition of the present invention may include a stannous ion source. The stannous ion source can be a soluble or an insoluble compound of stannous with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous. In some embodiments, the stannous ion source is selected from the group consisting of stannous chloride, stannous fluoride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof.

The oral care composition of the present invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care composition of the present invention may include a sweetener such as, for example, saccharin, for example sodium saccharin, acesulfame, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition. In some embodiments, the composition comprises sodium saccharin and sucralose. In a certain embodiment, the composition comprises a triple sweetener system of sodium saccharin, sucralose and rebaudioside M (Reb M).

The oral care composition of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The oral care composition of the invention may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations and mixtures thereof.

The oral care composition of the invention may include one or more pigments, such as whitening pigments. In some embodiments, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxyapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the teeth.

All ingredients for use in the compositions described herein should be orally acceptable. As used herein, "orally acceptable" may refer any ingredient that is present in a composition as described in an amount and form which does not render the composition unsafe for use in the oral cavity.

The invention provides a method of whitening teeth, comprising applying any of the oral care compositions disclosed herein, e.g., any of Compositions 1 et seq., to the surface of the teeth.

The invention provides the use of a block copolymer of ethylene oxide and propylene oxide for increasing the stability of an oral care composition comprising a peroxide whitening complex in an amount to provide from 3.5% to 7%, e.g., 3.5-6%, 3.5-5%, 3.5-4.5%, 3.8-4.2%, 3.9%-4.1%, or about 4%, of hydrogen peroxide by weight of the composition, wherein the block copolymer of ethylene oxide and propylene oxide is present in an amount of from 40% to 60% by weight of the composition. In some embodiments, the whitening complex comprises a cross-linked polyvinylpyrrolidone complexed with hydrogen peroxide (PVP-$H_2O_2$). In some embodiments, the block copolymer of ethylene oxide and propylene oxide has a molecular weight of from 1,000 Da to 3,000 Da. In some embodiments, the composition does not contain propylene glycol.

EXAMPLES

Example 1

In order to formulate stable oral care whitening compositions containing a high level (4%) of hydrogen peroxide, the interaction of cross-linked PVP complexed with hydrogen peroxide (PVP-$H_2O_2$) with different humectants was examined. PVP-$H_2O_2$ was mixed with a block copolymer of ethylene oxide and propylene oxide (PLURONIC® L35) or propylene glycol, as shown in Table 1. Weights of the materials were decided based on their formula percentages.

TABLE 1

|  | Mixture sample 1 | Mixture sample 2 |
| --- | --- | --- |
| Polyoxypropylene-Polyoxyethylene Block Copolymer (L35) | 10 g | 0 g |
| Propylene glycol | 0 g | 10 g |
| Cross-linked PVP complexed with Hydrogen Peroxide (18% hydrogen peroxide) | 4.4 g | 4.4 g |

The left and right vials in FIG. 1 show PVP-$H_2O_2$ mixed with PLURONIC® L35 and propylene glycol respectively. When PVP-$H_2O_2$ was mixed with PLURONIC® L35 (left vial), a homogeneous and smooth mixture was formed. However, the mixture of PVP-$H_2O_2$ and propylene glycol (right vial) was very viscous and a rough structure was obtained. It is believed that the distinct structures of the mixtures are mainly due to the different reactions of PVP-$H_2O_2$ with PLURONIC® L35 and Propylene glycol. PVP-$H_2O_2$ has little interaction with PLURONIC® L35, while PVP-$H_2O_2$ swells in propylene glycol.

Seven 4% $H_2O_2$ whitening toothpastes with various humectant systems were prepared as indicated in Table 2. Composition 1 contains 46.91% PLURONIC® L35 but does not contain propylene glycol. Compositions 2-5 contain various amounts of PLURONIC® L35 and propylene glycol. Compositions 6 and 7 contain 47.51% or 52.51% propylene glycol but do not contain PLURONIC® L35.

TABLE 2

|  | Comp. 1 | Comp. 2 | Comp. 3 | Comp. 4 | Comp. 5 | Comp. 6 | Comp. 7 |
| --- | --- | --- | --- | --- | --- | --- | --- |
| Polyoxypropylene-Polyoxyethylene Block Copolymer (L35) | 46.91% | 40% | 30% | 20% | 10% | 0 | 0 |
| Propylene glycol | 0% | 7.41% | 17.61% | 27.71% | 37.71% | 47.51% | 52.51% |
| Cross-linked PVP complexed with hydrogen peroxide (18% hydrogen peroxide) | 22% | 22% | 22% | 22% | 22% | 22% | 22% |
| Fumed Silica | 1% | 0.50% | 0.30% | 0.20% | 0.20% | 0.20% | 0.20% |
| Calcium pyrophosphate | 15% | 15% | 15% | 15% | 15% | 15% | 10% |
| Polyethylene Glycol/Polypropylene Glycol 116/66 Copolymer | 7.5% | 7.5% | 7.5% | 7.5% | 7.5% | 7.5% | 7.5% |
| Sodium lauryl phosphate | 2% | 2% | 2% | 2% | 2% | 2% | 2% |
| Tetrasodium pyrophosphate | 1.3% | 1.3% | 1.3% | 1.3% | 1.3% | 1.3% | 1.3% |
| Sodium monofluorophosphate | 0.76% | 0.76% | 0.76% | 0.76% | 0.76% | 0.76% | 0.76% |

TABLE 2-continued

|  | Comp. 1 | Comp. 2 | Comp. 3 | Comp. 4 | Comp. 5 | Comp. 6 | Comp. 7 |
|---|---|---|---|---|---|---|---|
| Sodium acid pyrophosphate | 0.4% | 0.4% | 0.4% | 0.4% | 0.4% | 0.6% | 0.6% |
| Sweeteners, antioxidant, flavor | 3.13% | 3.13% | 3.13% | 3.13% | 3.13% | 3.13% | 3.13% |
| Total components | 100% | 100% | 100% | 100% | 100% | 100% | 100% |

Formula processability of these toothpastes was evaluated by a lab pumping test. The lab pumping test is to evaluate whether a toothpaste can be transferred from a storage tank to a filling tank in the manufacturing facility. As a rule of thumb, a pressure lower than 15 bar is considered to be safe and operable in production. Physical formula stability was also evaluated. The results are shown in Table 3.

TABLE 3

|  | Pressure (bar) | Physical Stability |
|---|---|---|
| Comp. 1 | 7 | pass |
| Comp. 2 | 31 | Failed - too thick to dispense after 1 week/60° C. aging. Also failed the pumping test. |
| Comp. 3 | 46 | Failed - severe phase separation, too thick to dispense after 2 week/60° C. aging. Also failed the pumping test. |
| Comp. 4 | 77 | Failed - too thick to dispense after 2 week/60° C. aging. Also failed the pumping test. |
| Comp. 5 | 49 | Failed - too thick to dispense after 2 week/60° C. aging. Also failed the pumping test. |
| Comp. 6 | 62 | Failed - too thick to dispense after 1 week/60° C. aging. Also failed the pumping test. |
| Comp. 7 | 39 | Failed - too thick to pump in making line. |

Composition 1 containing PLURONIC® L35 exhibited an acceptable pressure (7 bar) in the lab pumping test and passed the physical stability test, while Compositions 2-5 containing a combination of PLURONIC® L35 and propylene glycol in various ratios and Compositions 6-7 containing propylene glycol were too thick to dispense upon aging and/or too thick to pump in making line. These results show that propylene glycol alone or a combination of PLURONIC® L35 and propylene glycol cannot be used as a humectant system for 4% $H_2O_2$ whitening toothpastes and the complete replacement of propylene glycol with a block copolymer of ethylene oxide and propylene oxide (PLURONIC® L35) improves the physical stability and processability of 4% $H_2O_2$ whitening toothpaste.

Example 2

Whitening toothpastes containing 1, 2, 3, or 4% $H_2O_2$ were prepared as indicated in Table 4.

TABLE 4

| Ingredient | Comp. 8 | Comp. 9 | Comp. 10 | Comp. 11 |
|---|---|---|---|---|
| Polyoxypropylene-Polyoxyethylene Block, L35 | 0% | 0% | 0% | 46.79% |
| Propylenge glycol | 34.16% | 40.13% | 52.78% | 0% |
| Polyethylelne glycol 600 | 10% | 10% | 0% | 0% |
| glycerin | 10% | 2.5% | 0% | 0% |
| Cross-linked PVP complexed with hydrogen peroxide (18% hydrogen peroxide) | 5.5% | 11% | 16.5% | 22% |
| Fumed Silica | 3.38% | 1.75% | 0.4% | 1.5% |
| Polyvinyl pyrrolidone | 3.38% | 1.75% | 0% | 0% |
| Polyethylene Glycol/Polypropylene Glycol | 10% | 10% | 7.5% | 7.5% |

TABLE 4-continued

| Ingredient | Comp. 8 | Comp. 9 | Comp. 10 | Comp. 11 |
|---|---|---|---|---|
| Sodium monofluorophosphate | 0.76% | 0.76% | 0.76% | 0.76% |
| Calcium pyrophosphate | 15% | 15% | 15% | 15% |
| Sodium lauryl phosphate | 2% | 2% | 2% | 2% |
| Tetrasodium pyrophosphate | 2% | 1.3% | 1.3% | 1.3% |
| Sodium acid pyrophosphate | 0.9% | 0.6% | 0.6% | 0.4% |
| Sweeteners, antioxidant, flavor | 2.93% | 3.21% | 3.16% | 2.75% |
| Total Components | 100% | 100% | 100% | 100% |

Composition 8-11 contain 1, 2, 3, or 4% hydrogen peroxide, as delivered from the cross-linked PVP complexed with hydrogen peroxide. A commonly used humectant, propylene glycol, was completely replaced by a block copolymer of ethylene oxide and propylene oxide (PLURONIC® L35) in Composition 11. Composition 11 contains 46.79% PLURONIC® L35 but does not contain propylene glycol as the orally acceptable vehicle. A triple sweetener system of Sodium Saccharin, Sucralose and BESTEVIA® Reb M was used in Composition 11 to provide a nice taste by countering the bitter taste of the block copolymer L35. The stability of Composition 11 was evaluated under accelerated aging conditions. Particularly, the composition was aged in an incubator maintained at 40° C. and 75% Relative Humidity or at 30° C. and 65% Relative Humidity for three months. Composition 11 showed acceptable physical stability.

The chemical stability of Compositions 8-11 was evaluated by determining the amount of hydrogen peroxide (HP) contained in the composition over time. As shown in Table 5, Compositions 8-11 exhibited good hydrogen peroxide stability.

TABLE 5

|  | % HP | | | |
|---|---|---|---|---|
| Aging Condition | Comp. 8 | Comp. 9 | Comp. 10 | Comp. 11 |
| 1 month, 40° C./75% RH | 0.96% | 1.90% | 2.90% | 4.02% |
| 2 months, 40° C./75% RH | 0.93% | 1.90% | 2.90% | 4.10% |
| 3 months, 30° C./65% RH |  |  |  | 4.14% |
| 3 months, 40° C./75% RH | 0.90% | 1.80% | 2.80% | 4.05% |

The chemical stability of Composition 11 was further evaluated by determining the amount of soluble fluoride contained in the composition over time.

TABLE 6

Soluble Fluoride Stability of Composition 11 Over Time

| Aging Condition | Soluble Fluoride, ppm |
|---|---|
| 1 month, 40° C./75% RH | 1080 |
| 2 months, 40° C./75% RH | 1050 |
| 3 months, 30° C./65% RH | 1090 |
| 3 months, 40° C./75% RH | 1100 |

As shown in Table 6, Composition 11 exhibited good fluoride stability. The amount of hydrogen peroxide and soluble fluoride in Composition 11 remained substantially constant over time under accelerated aging conditions.

The whitening efficacy of Composition 11 (4% HP toothpaste) was compared with Composition 10 (3% HP toothpaste). Whitening efficacy was determined by the standard brushing protocol using human molars in lab. Twenty human molars with physical soundness were selected and cleaned with ethanol and then washed by running tap water. The root of the teeth was removed using a saw machine and then cut in half with each half assigned to one product. The halved molar was mounted in resin with crown side exposed and kept flat as much as possible. The baseline L*, a*, b* of the halved molars were measured by two equipment, Hyperspectral Camera (Middleton Spectral Vision) and EasyShade (Vita) following respective operation manual. Hyperspectal camera measures the overall teeth whiteness, while EasyShade measures surface and underneath teeth whiteness separately. The molars were then placed in brushing trays, 4 pieces per tray, which were assembled in a brushing machine. The brushing machine was set to brush the molars at constant speed of 120 strokes/minute for 2 minutes each cycle. Toothpaste was made into 1:1 slurry in DI water and 20 ml of such slurry was used per tray per brushing cycle. Every two brushing cycles representing a day of use, the molars were measured again by three equipment on L*, a*, b*. Delta WIO (a tooth whitening index) was then calculated to show the whitening efficacy. The higher Delta WIO value indicates the better whitening performance. The results are shown in Tables 7 and 8.

TABLE 7

Results of Delta WIO from Hyperspectral Camera

| Time Point | Delta WIO of 3% HP Toothpaste | Delta WIO of 4% HP Toothpaste |
|---|---|---|
| Baseline | 0 | 0 |
| Day 1 | −0.04 | 2.55 |
| Day 2 | −0.22 | 3.79 |
| Day 3 | 0.65 | 7.44 |
| Day 4 | 2.55 | 7.85 |
| Day 5 | 2.82 | 9.02 |
| Day 6 | 4.06 | 9.98 |
| Day 7 | 7.27 | 11.85 |

TABLE 8

Results of Delta WIO from EasyShade

| | Delta WIO of 3% HP Toothpaste | | Delta WIO of 4% HP Toothpaste | |
|---|---|---|---|---|
| Time Point | Surface | Inside | Surface | Inside |
| Baseline | 0 | 0 | 0 | 0 |
| Day 1 | 2.77 | 0.81 | 3.83 | 3.81 |
| Day 2 | 3.76 | −0.94 | 8.73 | 4.78 |
| Day 3 | 4.79 | 1.92 | 11.34 | 3.83 |
| Day 4 | 5.16 | 3.01 | 12.06 | 4.92 |
| Day 5 | 4.41 | 3.94 | 11.67 | 5.78 |
| Day 6 | 6.35 | 3.66 | 13.21 | 7.06 |
| Day 7 | 5.84 | 3.01 | 13.23 | 7.30 |

As shown in Tables 7 and 8, 4% HP toothpaste (Composition 11) showed better whitening performance than 3% HP toothpaste (Composition 10) as seen in the data from both equipments. 4% HP toothpaste showed a significantly greater increase in WIO compared to 3% HP toothpaste. Furthermore, 4% HP toothpaste also outperformed 3% HP toothpaste in removing stains inside the teeth.

While the disclosure has been described with respect to specific examples including presently preferred modes of carrying out the disclosure, those skilled in the art will appreciate that there are numerous variations and permutations of the above described systems and techniques. It is to be understood that other embodiments may be utilized and structural and functional modifications may be made without departing from the scope of the present disclosure. Thus, the scope of the disclosure should be construed broadly as set forth in the appended claims.

The invention claimed is:

1. A composition comprising a peroxide whitening complex in an amount to provide from 3.5% to 7% of hydrogen peroxide by weight of the composition, and a block copolymer of ethylene oxide and propylene oxide in an amount of from 40% to 60% by weight of the composition.

2. The composition of claim 1, wherein the whitening complex comprises a cross-linked polyvinylpyrrolidone complexed with hydrogen peroxide (PVP-$H_2O_2$).

3. The composition of claim 1, wherein the peroxide whitening complex is present in an amount to provide from 3.8 to 4.2% of hydrogen peroxide by weight of the composition.

4. The composition of claim 1, wherein the block copolymer of ethylene oxide and propylene oxide is represented by formula

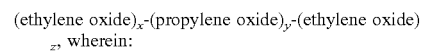

, wherein:

x is an integer from about 5 to about 15,
y is an integer from about 10 to about 20, and
z is an integer from about 5 to about 15.

5. The composition of claim 1, wherein the block copolymer of ethylene oxide and propylene oxide is represented by formula (ethylene oxide)$_{11}$-(propylene oxide)$_{16}$-(ethylene oxide)$_{11}$.

6. The composition of claim 1, wherein the block copolymer of ethylene oxide and propylene oxide has an average molecular weight of from 1,000 Da to 3,000 Da.

7. The composition of claim 1, wherein the block copolymer of ethylene oxide and propylene oxide is present in an amount of from 44% to 50% by weight of the composition.

8. The composition of claim 1, wherein the composition does not contain propylene glycol.

9. The composition of claim 1, wherein the composition does not contain any of propylene glycol, glycerin, sorbitol and polyethyleneglycol (PEG).

10. The composition of claim 1, wherein the composition comprise a thickening agent selected from fumed silica, colloidal silica, cetearyl alcohol, or a combination thereof.

11. The composition of claim 1, wherein the composition comprises an ethylene oxide, propylene oxide block co-polymer having an average molecular weight of greater than 5000 Da.

12. The composition of claim 1, wherein the composition comprises a fluoride ion source.

13. The composition of claim 1, wherein the composition comprises an abrasive selected from sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, or mixtures thereof.

14. The composition of claim 1, wherein the composition comprises an anionic surfactant.

15. The composition of claim 1, wherein the composition comprises an anticalculus agent selected from tetrasodium pyrophosphate (TSPP), sodium tripolyphosphate (STPP), or a combination thereof.

16. The composition of claim 1, wherein the composition comprises sodium acid pyrophosphate.

17. The composition of claim 1, wherein the composition the composition comprises sodium saccharin and sucralose.

18. The composition of claim 1, wherein the composition is free or substantially free of water.

19. The composition of claim 1, wherein the composition is a toothpaste or gel.

20. A method of whitening teeth, comprising applying an oral care composition according to claim 1 to the surface of the teeth.

\* \* \* \* \*